(12) United States Patent
Ferree

(10) Patent No.: US 6,371,990 B1
(45) Date of Patent: Apr. 16, 2002

(54) ANNULUS FIBROSIS AUGMENTATION METHODS AND APPARATUS

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 5 days.

(21) Appl. No.: 09/690,536

(22) Filed: Oct. 16, 2000

Related U.S. Application Data

(63) Continuation-in-part of application No. 09/638,726, filed on Aug. 14, 2000, and a continuation-in-part of application No. 09/415,382, filed on Oct. 8, 1999.
(60) Provisional application No. 60/159,488, filed on Oct. 14, 1999.

(51) Int. Cl.[7] .................................................. A61F 2/44
(52) U.S. Cl. ..................................... 623/17.16; 623/908
(58) Field of Search ........................... 623/17.11, 17.12, 623/17.16, 908; 128/898; 606/69

(56) References Cited

U.S. PATENT DOCUMENTS

| | | | |
|---|---|---|---|
| 6,183,518 B1 * | 2/2001 | Ross et al. ................ | 623/17.16 |
| 6,187,048 B1 * | 2/2001 | Milner et al. ............. | 623/17.12 |
| 6,221,109 B1 * | 4/2001 | Geistlich et al. .......... | 623/17.11 |
| 6,231,615 B1 * | 5/2001 | Preissman ................ | 623/23.73 |

* cited by examiner

*Primary Examiner*—David H. Willse
*Assistant Examiner*—Suzette J. Jackson
(74) *Attorney, Agent, or Firm*—Gifford, Krass, Groh, Sprinkle, Anderson & Citkowski, PC

(57) ABSTRACT

Apparatus and methods aid the annulus in controlling vertebral motion, thereby preventing additional annular tears, and decreasing pain from annular tears. A biocompatible fabric or mesh is attached to the annulus. The material may be attached to the inside and/or outside of the annulus by stitches, staples, adhesives, or other suitable techniques. Alternatively, the fabric may be attached to the vertebra above and below the disc by screws, staples, tacks, or porous material for bone ingrowth such as titanium.

19 Claims, 3 Drawing Sheets

ANNULUS FIBROSIS AUGMENTATION METHODS AND APPARATUS

REFERENCE TO RELATED APPLICATIONS

This application claims priority from U.S. provisional application Ser. No. 60/159,488, filed Oct. 14, 1999, and is a continuation-in-part of U.S. patent application Ser. Nos. 09/638,726, filed Aug. 14, 2000; and 09/415,382, filed Oct. 8, 1999, the entire contents of each application being incorporated herein by reference.

FIELD OF THE INVENTION

This invention relates generally to human spinal surgery and, in particular, to methods and apparatus for augmenting the annulus fibrosis while controlling vertebral motion, thereby preventing additional annular tears and attendant discomfort.

BACKGROUND OF THE INVENTION

According to human anatomy, spinal function is dependent upon the intervertebral disc and the facet joints. In a sense, the annulus fibrosis, nucleus pulpous, and the facet joints form the legs of a three-legged stool.

To restore disc height resulting, for example, from degenerative disease, prosthetic discs are used to replace only the nucleus pulpous. Reference is made to my co-pending patent application Ser. No. 091,415,382, which discusses spinal anatomy, spinal physiology, disc degeneration, surgical and non-surgical treatments of disc disease, and the advantages of prosthetic disc replacement.

The annulus is formed of 10 to 60 fibrous bands which serve to control vertebral motion. One half of the bands tighten to check motion when the vertebra above or below the disc are turned in either direction. Restoring disc height returns tension to the annular noted in the prosthetic disc patent application. In addition, restoring annular tension decreases annular protrusion into the spinal canal or neural foramen. Thus, decreasing annular protrusion may eliminate pressure on the spinal cord or nerve roots.

At times the rotational, translational, and axial compression forces exceed the strength of the annular fibers. The excessive forces tear the annular fibers. A single event can tear one band to all the bands. Subsequent tears can connect to previous tears of a few bands resulting in a hole through the entire annulus fibrosis. Holes through the entire annulus fibrosis can result in extrusion of the nucleus pulpous. Extrusion of the nucleus pulpous is referred to as a "herniated disc." Disc herniation can result in back pan, neck pain, arm pain, leg pain, nerve or spinal cord injury, or a combination of the above.

Since the annulus is innervated with pain fibers, acute annular tears without herniation of the nucleus can be painful. Unfortunately, the annular tears often do not heal completely. The chronic tears can result in neck pain, back pain, shoulder pain, buttock pain, or thigh pain. The chronic tears weaken the annulus fibrosis predisposing the disc to herniation or additional annular tears. My co-pending U.S. patent applications, Ser. No. 09/638,726, entitled "Methods and Apparatus for Treating Disc Herniation," and 09/415,382, entitled "Artificial Intervertebral Disc Replacement" describe methods and apparatus for occluding annular defects.

Prosthetic replacement of the nucleus pulpous alone risks future problems arising from annular tears. Patients may continue to complain of pain from the stresses placed onto the weakened annulus. Secondly, tears of the annulus could result in extrusion of the prosthetic nucleus. In addition, remaining nucleus pulpous could herniate through annular tears.

Some prosthetic disc designs attempt to replace nucleus and annular functions. In general, these designs attach the prosthetic disc to the vertebrae. Many of the techniques in this area attach the prosthetic disc to the end plates of the vertebrae with screws, spikes, flanges, or porous surfaces for bone ingrowth. My co-pending U.S. patent application Ser. Nos. 09/322,516 and 09/415,382 describe methods and devices to assist the annulus in retaining remaining nucleus pulpous and a prosthetic nucleus. The entire contents of these applications are incorporated herein by reference.

The need remains, however, for a more extensive annulus augmentation technique. Failure at the disc vertebra interface could result in loosening of the prosthesis, however, and patients with loose prosthetic discs would likely require revision surgery.

SUMMARY OF THE INVENTION

This invention broadly resides in devices to augment the annulus fibrosis. More specifically, the present invention serves to aid the annulus in controlling vertebral motion, thereby preventing additional annular tears, and decreasing pain from annular tears. In contrast to previous designs, the devices would also assist a larger area of annulus, if not the entire annulus.

Devices according to the invention augment the annulus fibrosis and/or the annulus fibrosis attachment to the vertebrae above and below the disc. In the preferred embodiment, this is accomplished in at least two ways. First a biocompatible fabric or mesh such as Gore-Tex or Dacron is attached to the annulus. The material may be attached to the inside and/or outside of the annulus by stitches, staples, adhesives, or other suitable techniques. Alternatively, the fabric may be attached to the vertebra above and below the disc by screws, staples, tacks, or porous material for bone ingrowth such as titanium. Other methods of attachment to the annulus or vertebrae would also be acceptable if the overall goals of the invention are otherwise achieved.

DETAILED DESCRIPTION OF THE INVENTION

FIGS. 1A through 1E illustrate the steps associated with preferred apparatus and methods according to the invention.

Figure 1A:
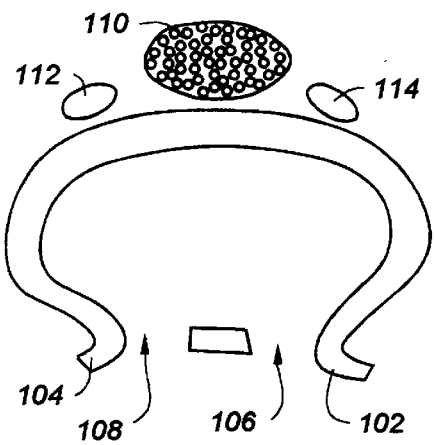
FIG. 1A is a cross-section of an intervertebral disc used to illustrate an initial step according to a method annulus augmentation according to the invention.
Figure 1B:
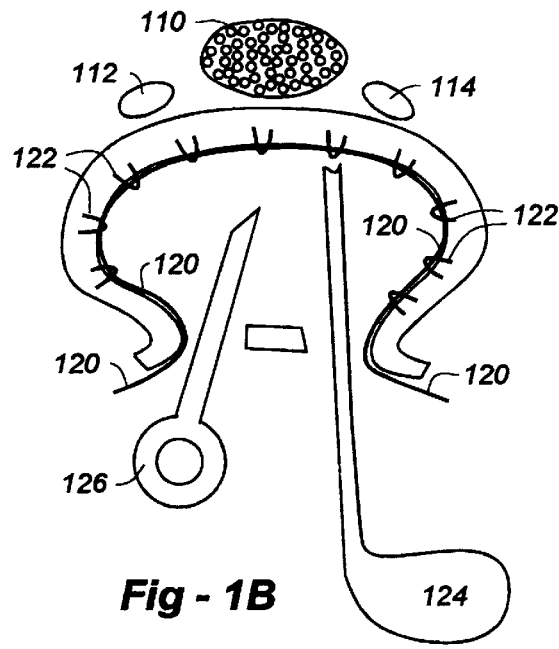
FIG. 1B illustrates the step of fastening an annular mesh inside the disc space.
Figure 1C:
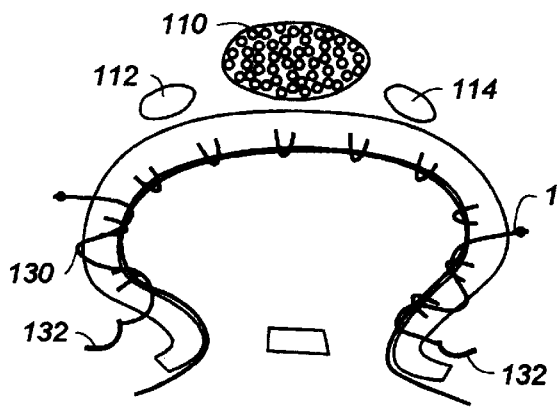
FIG. 1C illustrates the step of anterior annulus augmentation.
Figure 1D:
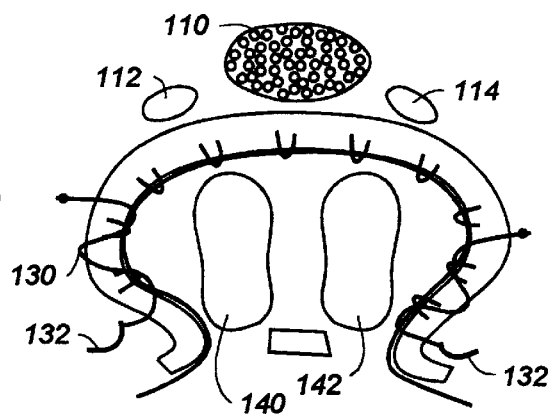
FIG. 1D illustrates the step of prosthetic disc replacement.
Figure 1E:
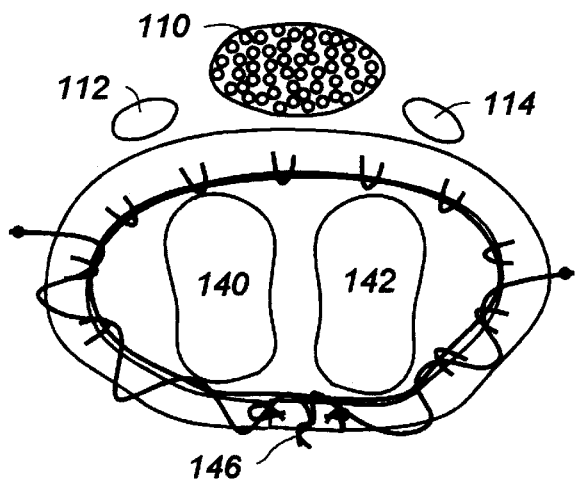
FIG. 1E is a drawing which shows the step of closing the annular flaps used to insert the disc replacement prostheses.
Figure 1F:
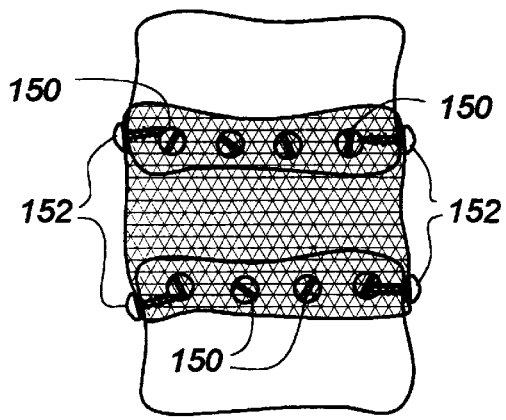
FIG. 1F is a frontal view drawing of the completed repair following the steps of FIGS. 1A through 1E.
Figure 2:
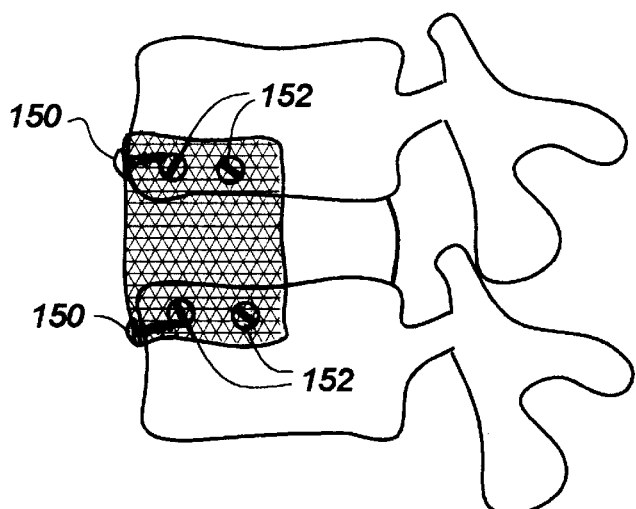
FIG. 2 is a side-view drawing of the completed augmentation according to the steps of FIGS. 1A through 1E.

FIG. 1F is a frontal view of a completed annulus augmentation, and FIG. 2 is a side view of the overall repair. Overall, the augmentation is performed through the abdomen after preparation for the insertion of a prosthetic nucleus.

FIG. 1A illustrates annular flaps 102 and 104 formed in the annulus, creating annular holes 106 and 108, into which prosthetic disc replacements will be inserted. The sack of nerve roots is shown generally at 110, 112 and 114.

FIG. 1B illustrates how, according to a preferred method of the invention, the inner wall of the annulus is reinforced through the use of a mesh 120 stapled from within the disc space using staples 122. A stapling device similar to that used in laproscopic procedures may be used. Note that the staples preferably penetrate only a portion of the nucleus, thereby protecting the structures on the other side of the annulus. In addition to the stapling device 124, a separate device 126 may be used to provide laproscopic assistance. Having staples a mesh, screen or other suitable material to the inner wall of the annulus, an anterior annulus augmentation 130 is sewn to the posterior material using a needle and suture 132. In FIG. 1D, the nucleus replacement prosthesis are introduced. Although a pair of adjoining prosthetic devices 140 and 142 are shown, those of skill in the art of spinal surgery will understand that more or fewer devices, potentially affecting the number of requisite flaps, may alternative be utilized.

In FIG. 1E, the flaps having been sewn shut using stitches 146 as appropriate to a staple closure. FIG. 1F illustrates the preferred additional but optional use of a screws 150 used to hold the mesh in place relative to the adjacent vertebrae. FIG. 2 is a side-view illustrating the preferred use of lateral screws 152 in addition to anterior screws 150.

As mentioned in the Summary of the Invention, the mesh may be any appropriate material such as Gortex, nylon, and other flexible biocompatible materials. To add additional strength, such materials may be combined with a biologic tissue such as treated pig intestine, or a material to promote tissue ingrowth, such as collagen.

Figure 3A:
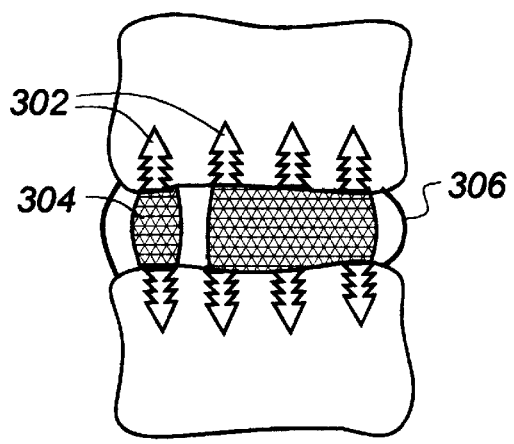
FIG. 3A is a side-view drawing of an alternative augmentation according to the invention.
Figure 3B:
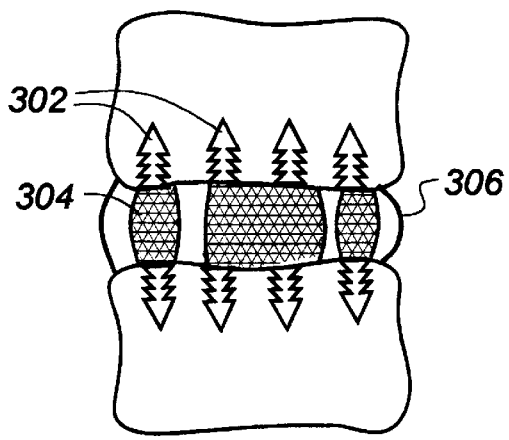
FIG. 3B is a frontal view of the augmentation.

FIG. 3A is a drawing which shows a side view of an alternative embodiment according to the invention, wherein titanium spikes 302 are used to promote bone ingrowth. A braided or mesh material 304, which again can take the form of Gortex, nylon, or other suitable flexible materials, is dressed over the annulus 306 and attached to one or both of the adjacent vertebrae through any suitable means.

Figure 4A:
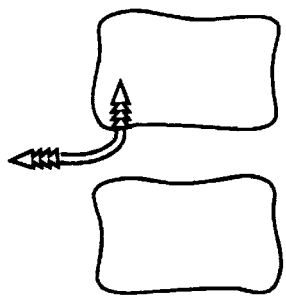
FIG. 4A is a drawing which shows an initial step according to the different annulus augmentation embodiment utilizing a spike forced into adjacent vertebrae.
Figure 4B:
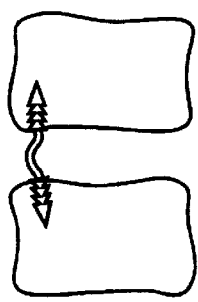
FIG. 4B is an intermediate step of this alternative method, wherein the spike is introduced into adjacent vertebrae.
Figure 4C:
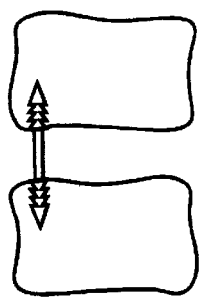
FIG. 4C is a drawing which shows the spike, having been straightened into the adjacent vertebrae.

FIG. 4A illustrates an initial step according to an alternative embodiment of the invention, wherein a spike of a biocompatible material such as titanium is forced into upper and lower vertebrae so as to fortify the annulus. FIG. 4A shows the spike being inserted into one vertebrae, FIG. 4B shows the spike being introduced into the plate of the opposing vertebrae, and FIG. 4C illustrates the spike in a straightened out condition. Depending upon the magnitude of the defect, multiple spikes may be used to ensure a stable repair.

I claim:

1. A method of fortifying an annulus fibrosis having an inner wall and an outer wall between adjacent vertebrae with opposing endplates, the method comprising the steps of:

forming a hole through the annulus sufficient to access the inner wall;

covering at least a portion of the inner wall with a first layer of flexible, biocompatible material;

fastening the first layer of material to the inner wall of the annulus at one or more points; and closing the hole in the annulus.

2. The method of claim 1, further including the steps of:

covering a portion of the outer wall with a second layer of flexible, biocompatible material, at least in the region where the hole was closed in the annulus; and fastening the second layer of material to the outer wall of the annulus at one or more points.

3. The method of claim 1, further including the step of fastening the second layer of material at one or more points of the adjacent vertebrae.

4. The method of claim 1, wherein the step of fastening the first layer of material to the inner wall of the annulus includes the use of staples or fasteners which do not penetrate through to the outer wall.

5. The method of claim 1, wherein the step of fastening the second layer of material to the outer wall of the annulus includes the use of sutures or fasteners which penetrate the annulus and engage with the first layer of material.

6. The method of claim 1, further including the step of inserting a prosthetic disc replacement into the hole in the annulus prior to closure.

7. The method of claim 1, wherein the first or second materials are mesh materials.

8. The method of claim 1, further including the step of attaching a biologic material to the one or both of the layers of material to promote tissue ingrowth.

9. The method of claim 1, further including the step of attaching one or more pieces of porous in-growth material to one or both of the adjacent vertebrae.

10. In disc-replacement surgery of the type wherein one or more prosthetic disc elements are inserted into an intervertebral disc space through an annulus fibrosis having an inner wall and an outer wall between adjacent vertebra, the method comprising:

lining at least a portion of the inner wall of the annulus fibrosis with a layer of flexible, biocompatible material as a protective barrier against tearing.

11. The improvement of claim 10, wherein the material is a mesh or a screen.

12. The improvement of claim 10, including the step of fastening the layer of material to the inner wall of the annulus fibrosis.

13. The improvement of claim 12, including the step of fastening the layer of material to the inner wall with fasteners that do not penetrate through to the outer wall.

14. The improvement of claim 12, further including the step of lining a portion of the outer wall with a second layer of flexible, biocompatible material, at least in the region where the prosthetic disc elements are inserted through the annulus fibrosis into the intervertebral disc space.

15. The improvement of claim 14, further including the step of fastening the second layer of material to the outer wall of the annulus at one or more points.

16. The improvement of claim 14, further including the step of fastening the second layer of material at one or more points of the adjacent vertebrae.

17. The improvement of claim 16, wherein the step of fastening the second layer of material to the outer wall of the annulus includes the use of fasteners which penetrate the annulus and engage with the first layer of material.

18. The improvement of claim 14, further including the step of attaching a biologic material to the one or both of the layers of material to promote tissue ingrowth.

19. The improvement of claim 10, further including the step of attaching one or more pieces of porous in-growth material one or both of the adjacent vertebrae.

* * * * *